(12) United States Patent
Faircloth et al.

(10) Patent No.: US 7,473,681 B2
(45) Date of Patent: Jan. 6, 2009

(54) KAHALALIDE F

(75) Inventors: Glynn Thomas Faircloth, Cambridge, MA (US); Bastiaan Nuijen, Amsterdam (NL); Steve Weitman, San Antonio, TX (US)

(73) Assignee: Pharma Mar, S.A., Madrid (ES)

(*) Notice: Subject to any disclaimer, the term of this patent is extended or adjusted under 35 U.S.C. 154(b) by 519 days.

(21) Appl. No.: 10/399,571

(22) PCT Filed: Oct. 31, 2001

(86) PCT No.: PCT/GB01/04821

§ 371 (c)(1),
(2), (4) Date: Nov. 14, 2003

(87) PCT Pub. No.: WO02/36145

PCT Pub. Date: May 10, 2002

(65) Prior Publication Data

US 2004/0067895 A1 Apr. 8, 2004

Related U.S. Application Data

(60) Provisional application No. 60/348,449, filed on Oct. 19, 2001, provisional application No. 60/246,299, filed on Nov. 6, 2000, provisional application No. 60/244,471, filed on Oct. 31, 2000.

(51) Int. Cl.
*A61K 38/00* (2006.01)
(52) U.S. Cl. ........................................... 514/11
(58) Field of Classification Search .................. 514/2, 514/9, 11, 460
See application file for complete search history.

(56) References Cited

U.S. PATENT DOCUMENTS

| 5,037,644 A | * | 8/1991 | Shaked et al. ............... 424/85.2 |
| 5,849,704 A | * | 12/1998 | Sorensen et al. ............... 514/12 |
| 6,011,010 A | * | 1/2000 | Scheuer et al. ............... 514/11 |
| 2005/0054555 A1 | | 3/2005 | Jimeno et al. |

FOREIGN PATENT DOCUMENTS

| EP | 0 357 296 | 8/1989 |
| EP | 0 448 146 | 9/1991 |
| EP | 0 610 078 A1 | 8/1994 |
| EP | 0 827 751 | 3/1998 |
| EP | 0 838 221 A1 | 4/1998 |
| JP | 05097703 | 4/1993 |
| JP | 05194265 | 8/1993 |
| JP | 07076525 | 3/1995 |
| JP | 10014581 | 1/1998 |
| WO | WO 93/11771 | 6/1993 |
| WO | WO 97/25977 | 7/1997 |
| WO | WO 99/42125 | 8/1999 |
| WO | WO 99/52524 | 10/1999 |
| WO | WO 00/16794 | 3/2000 |
| WO | WO 01/58934 | 8/2001 |

OTHER PUBLICATIONS

Goodman & Gilman's, The Pharmacological Basis of Therapeutics, Ninth Edition, McGraw Hill, New York (1996), Section X, Chemotherapy of Neoplastic Diseases, pp. 1225-1229.*

Nuijen et al., Development of a lyophilized parenteral pharmaceutical formualtion of the investigational polypeptide marine anticancer agent kahalalide F, (2001), vol. 27, No. 8, pp. 767-780 (22 ref.), printer pp. 1 and 2, especially page 1.*

El Sayed, Khalid A. et al., "The Marine Environment: A Resource for Prototype Antimalarial Agents", *Journal of Natural Toxins*, vol. 5, No. 2, pp. 261-285 (1996).

Garcia-Rocha, Mar et al., "The antitumoral compound Kahalalide F acts on cell lysosomes", *Cancer Letters*, vol. 99, No. 1, pp. 43-50 (1996).

Goetz, Gilles et al., "The Absolute Stereochemistry of Kahalalide F", *Tetrahedron*, vol. 55, pp. 7739-7746 (1999).

Goetz, G. et al., "Two Acyclic Kahalalides from the Sacoglossan Mollusk Elysia rufescens[1]", *Journal of Natural Products*, vol. 60, No. 6, pp. 562-567 (1997).

Hamann, Mark T. et al., "Kahalalides F: A Bioactive Depsipeptide from the Sacoglossan Mollusk Elysia refuscens and the Green Alga Bryopsis sp.[1]", *Journal of the American Chemical Society*, vol. 115, No. 13, pp. 5825-5826 (1993).

Hamann, Mark T. et al., "Kahalalides: Bioactive Peptides from a Marine Mollusk Elysia refuscens and Its Algal Diet Bryopsis sp[1]", *Journal of Organic Chemistry*, vol. 61, No. 19, pp. 6594-6600 (1996).

Hamann, Mark T. et al., "Kahalalides: Bioactive Peptides from a Marine Mollusk Elysia refuscens and Its Algal Diet Bryopsis sp.[1]", *The Journal of Organic Chemistry*, vol. 63, No. 14, pp. 4856 (1998).

Horgen, F. David et al., "A New Depsipeptide from the Sacoglossan Mollusk Elysia ornate and the Green Alga Bryopsis Species[1]", *Journal of Natural Products*, vol. 63, No. 1, pp. 152-154 (2000).

(Continued)

Primary Examiner—Shengjun Wang
Assistant Examiner—Timothy E Betton
(74) Attorney, Agent, or Firm—Fish & Richardson P.C.

(57) ABSTRACT

Formulations and uses of kahalalide F.

7 Claims, No Drawings

OTHER PUBLICATIONS

Kan, Yukiko et al., "Kahalalide K: A New Cyclic Depsipeptide from the Hawaiian Green Alga Bryopsis Species", *Journal of Natural Products,* vol. 62, No. 8, pp. 1169-1172 (1999).

Lopez-Macia, Angel et al., "Kahalalide B. Synthesis of a natural cyclodepsipeptide", *Tetrahedron Letters,* vol. 41, pp. 9765-9769 (2000).

Nuijen, B. et al., "Development of a Lyophilized Parenteral Pharmaceutical Formulation of the Investigational Polypeptide Marine Anticancer Agent Kahalalide F", *Drug Development and Industrial Pharmacy,* vol. 27, No. 8, pp. 767-780 (2001).

"A Business Resource for Hawaii's Growth Industries, UH Biotechnology: Blockbuster Drugs Ahead?", 2000, http://www.tigrnet.org/tigr/reports/04 00issue.html.

Robinson, A., "Trawling for Cancer Cures", 1999, http://businessweek.com/1999_37/b3646225.htm.

Nuijen et al., "Pharmaceutical Development of a Parenternal Lyophilized Formulation of the Novel Antitumor Agent Aplidine", J. Pharma Sci. Technol., 2000, vol. 54, No. 3, pp. 193-208.

Wu et al., "The Formation oand Mechanism of Multimerization in a Freeze-Dried Peptide", Int. J. Pharma, 2000, vol. 200, No. 1, pp. 1-16.

* cited by examiner

KAHALALIDE F

CROSS REFERENCE TO RELATED APPLICATIONS

This application is the National Stage of International Application No. PCT/GB01/04821, filed on Oct. 31, 2001, which claims the benefit of prior U.S. Provisional Application 60/244,471, filed on Oct. 31, 2000; U.S. Provisional Application 60/246,229, filed on Nov. 6, 2000; and U.S. Provisional Application 60/348,449, filed on Oct. 19, 2001.

The present invention relates to kahalalide F, a peptide isolated from a herbivorous marine species of mollusc, *Elysia rufescens*.

BACKGROUND OF THE INVENTION

Kahalalide F is the subject of European Patent 610,078. The patent reports activity against in vitro cell cultures of human lung carcinoma A-549 and human colon carcinoma HT-29.

More information concerning kahalalide F is to be found, for example, in:

The absolute stereochemistry of kahalalide F. Goetz, Gilles; Yoshida, Wesley Y.; Scheuer, Paul J. Dep. Chemistry, Univ. Hawaii, Honolulu, Hi., USA. Tetrahedron (1999), 55(25), 7739-7746.

[Erratum to document cited in CA131:157974]. Tetrahedron (1999), 55(40), 11957.

Kahalalides: bioactive peptides from a marine mollusk *Elysia rufescens* and its algal diet *Bryopsis* sp. Hamann, Mark T.; Otto, Clifton S.; Scheuer, Paul J.; Dunbar, D. Chuck. Department of Chemistry, University of Hawaii of Manoa, Honolulu, Hi., USA. J. Org. Chem. (1996), 61(19), 6594-6600.

[Erratum to document cited in CA125:190997]. J. Org. Chem. (1998), 63(14), 4856.

The marine environment: A resource for prototype antimalarial agents. El Sayed, Khalid A.; Dunbar, D. Charles; Goins, D. Keith; Cordova, Cindy R.; Perry, Tony L.; Wesson, Keena J.; Sanders, Sharon C.; Janus, Scott A.; Hamann, Mark T. Center the Development Natural Products, University Mississippi, University, Miss., USA. J. Nat. Toxins (1996), 5(2), 261-285.

The antitumoral compound Kahalalide F acts on cell lysosomes. Garcia-Rocha, Mar; Bonay, Pedro; Avila, Jesus. 28049-Madrid, Spain. Cancer Lett. (Shannon, Irel.) (1996), 99(1), 43-50.

Kahalalide F: a bioactive depsipeptide from the sacoglossan mollusk *Elysia rufescens* and the green alga *Bryopsis* sp. Hamann, Mark T.; Scheuer, Paul J. Dep. Chem., Univ. Hawaii, Honolulu, Hi., USA. J. Am. Chem. Soc. (1993), 115(13), 5825-6.

SUMMARY OF THE INVENTION

We provide new formulations and new uses of kahalalide F.

PREFERRED EMBODIMENTS

A combination of a non-ionic surfactant and an organic acid is suited for use with a bulking agent to give a lyophilised form of kahalalide F suited for reconstitution. Reconstitution is preferably effected with a mix of emulsifying solubiliser, alkanol and water.

The lyophilised composition preferably comprises mainly the bulking agent, such as at least 90% or at least 95% bulking agent. Examples of bulking agents are well known and include sucrose and mannitol. Other bulking agents can be employed.

The non-ionic surfactant in the lyophilised composition is preferably a sorbitan ester, more preferably a polyethylene sorbitan ester, such as a polyoxyethylene sorbitan alkanoate, especially a polyoxyethylene sorbitan mono-oleate, for example polysorbate 80. The non-ionic surfactant typically comprises a few % of the composition, such as 0 to 5% of the composition, for instance 2 to 3% of the composition.

The organic acid in the lyophilised composition is typically an aliphatic acid, preferably a hydroxycarboxylic acid and more preferably a hydroxypolycarboxylic acid, notably citric acid. The organic acid typically comprises a few % of the composition, such as 0 to 5% of the composition, for instance 2 to 3% of the composition.

The amount of kahalalide F in the lyophilised composition is typically less than 1%, or often less than 0.1%, of the mix. A suitable amount is in the range 50 to 200 µg, say about 100 µg, per 100 mg of composition.

The emulsifying solubiliser for the reconstituting agent suitably comprises an polyethylene glycol ester, notably an ester of a fatty acid, more preferably a PEG oleate such as PEG-35 oleate. The emulsifying solubiliser is suitably 0 to 10% of the reconstituting agent, typically about 3 to 7%, say about 5%. The alkanol is usually ethanol, and is suitably 0 to 10% of the reconstituting agent, typically about 3 to 7%, say about 5%. The remainder of the reconstituting agent is water, and gives a reconstituted solution suited for intravenous injection.

Further dilution of the reconstituted solution with 0.9% saline may be appropriate for infusion of the kahalalide F.

In a particularly preferred embodiment, the lyophilised composition comprises 100 µg kahalalide F; 75 to 125 mg, especially 100 mg, bulking agent; 1 to 3 mg, especially about 2 mg of acid; and 1 to 3 mg, especially about 2 mg, of non-ionic surfactant.

The preferred reconstituting agent then comprises 2 to 7%, say about 5%, emulsifying solubiliser; 2 to 7%, say about 5%, alcohol; and remainder water.

The invention additionally provides kits comprising separate containers containing the lyophilised composition and the reconstituting agent. Methods of reconstitution are also provided.

The present invention further provides a method of treating any mammal, notably a human, affected by cancer which comprises administering to the affected individual a therapeutically effective amount of a pharmaceutical composition thereof prepared by reconstitution of a lyophilised composition of this invention. The present invention can be employed particularly for treatment of patients with refractory cancers that do not respond favourably to other treatments. In particular, the compositions of this invention can be employed after other chemotherapy has been tried and not worked.

In one embodiment, the reconstituted solution is prepared for infusion and is administered in a 3-hour infusion on concentrations of up to around 20 or 25 µg/ml, typically up to 15 µg/ml. Suitable infusion equipment preferably includes a glass container, rather than one of polyethylene. Tubing is preferably of silicone.

A further aspect of this invention resides in new uses for kahalalide F. In particular, we envisage its use against prostate cancer and in particular androgen-independent prostate cancer, breast cancer, colon cancer, non-small cell lung cancer, ovarian cancer and for treating neuroblastoma. Kahalalide F is also active against dedifferentiated and mesenchymal chodrosarcomas and osteosarcomas. The new reconstituted formulations provided by this invention maybe employed for the new uses, though other compositions are possible.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. In an alternative dosing protocol, the kahalalide F is administered for say about 1 hour for 5 consecutive days every 3 weeks. Other protocols can be devised as variations.

Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:
a) drugs with antimitotic effects, especially those which target cytoskeletal elements, including microtubule modulators such as taxane drugs (such as taxol, paclitaxel, taxotere, docetaxel), podophyllotoxins or yinca alkaloids (vincristine, vinblastine);
b) antimetabolite drugs such as 5-fluorouracil, cytarabine, gemcitabine, purine analogues such as pentostatin, methotrexate);
c) alkylating agents such as nitrogen mustards (such as cyclophosphamide or ifosphamide);
d) drugs which target DNA such as the antracycline drugs adriamycin, doxorubicin, pharmorubicin or epirubicin;
e) drugs which target topoisomerases such as etoposide;
f) hormones and hormone agonists or antagonists such as estrogens, antiestrogens (tamoxifen and related compounds) and androgens, flutamide, leuprorelin, goserelin, cyprotrone or octreotide;
g) drugs which target signal transduction in tumour cells including antibody derivatives such as herceptin;
h) alkylating drugs such as platinum drugs (cis-platin, carbonplatin, oxaliplatin, paraplatin) or nitrosoureas;
i) drugs potentially affecting metastasis of tumours such as matrix metalloproteinase inhibitors;
j) gene therapy and antisense agents;
k) antibody therapeutics;
l) other bioactive compounds of marine origin, notably the didemnins such as aplidine or ecteinascidins such as Et 743.

EXAMPLES OF THE INVENTION

Experimental work which underlies the present invention is described in the following Examples.

Example 1

Development of a Lyophilized, Parenteral Pharmaceutical Formulation of Kahalalide F, KF The purpose of this study was to develop a stable parenteral formulation of KF to be used in early clinical studies.

Methods. Solubility and stability of KF were studied as a function of polysorbate 80 (P80; 0.1-0.5% w/v) and citric acid monohydrate (CA; 5-15 mM) concentrations using an experimental design approach. Stabilities of KF lyophilized products containing crystalline (mannitol) or amorphous (sucrose) bulking agents were studied at +5° C. and +30° C. in the dark. Lyophilized products were characterized by infrared (IR) spectroscopy and differential scanning calorimetry. Recovery studies after reconstitution of KP lyophilized product and further dilution in infusion fluid were carried out to select an optimal reconstitution vehicle.

Results. It was found that a combination of P80 and CA is necessary to solubilize KF. Lyophilized products were considerably less stable with increasing P80 and CA concentrations, with the P80 concentration being the major effector. A combination of 0.1% w/v P80 and 5 mM CA was selected for further investigation. Lyophilized products containing sucrose as bulking agent were more stable compared to the products containing mannitol. The glass transition temperature of the sucrose-based product was determined to be +46° C. The amorphous state of the product was confirmed by IR analysis. A solution composed of Cremophor EL ethanol and Water for Injection (5/5/90% v/v/v CEW) kept KF in solution after reconstitution and further dilution with 0.9% NaCl (normal saline) down to 0.5 µg/mL.

Conclusions. A stable lyophilized formulation is presented containing 100 µg of kahalalide F, 100 mg sucrose, 2.1 mg CA and 2 mg P80 to be reconstituted with a vehicle composed of 5/5/90% v/v/v CEW, and to be further dilute using normal saline.

Example 2

Compatibility and Stability of Kahalalide F in Infusion Devices

Kahalalide F is pharmaceutically formulated as lyophilized products containing 50-150 µg active substance per dosage unit. Prior to in i.v. administration it is reconstituted with a solution composed of Cremophor EL, ethanol absolute and Water for Injection (CEW, 5/5/90% v/w) with further dilution in 0.9% w/v sodium chloride for infusion. The aim of this study was to investigate the compatibility and stability of kahalalide F with different infusion systems prior to the start of clinical trials. Due to the presence of Cremophor EL in the infusion solution, leaching of diethylhexlphthalate from polyvinyl chloride infusion containers (PVC, Add-a-Flex®) was found. Loss of kahalalide F as a consequence of sorption to contact surfaces was shown with an infusion container composed of low density polyethylene (LD-PE, Miniflac®).

We conclude that kahalalide F must be administered in a 3-hour infusion in concentrations of 0.5 µg/mL to 14.7 µg/mL using an administration set consisting of a glass container and silicone tubing. Kahalalide F 150 µg vial powder for infusion reconstituted with 5/5/90% v/v/v CEW is stable in the original container for at least 24 hours at room temperature (+20-25° C.) and ambient light conditions. Infusion solutions stored in glass infusion containers at either room temperature (+20-25° C., in the dark) or refrigerated conditions (+2-8° C., in the dark) are stable for at least 5 days after preparation.

Example 3

In Vitro Safety Toxicology of Kahalalide F

We have assessed the potential for toxicity of Kahalalide F, a compound derived from the Hawaiian mollusk, *Ellysia rubefescens* shown to have potent chemotoxic effects against prostate and neu~1 (Hcr2 overexpressing) breast tumor cells.

Using the CellTiter96 (MTS, Promega) in vitro cytoxicity assay, Kahalalide exhibits little toxicity against cardiac (H9 c2 (2-1)) or skeletal muscle (L8) cells ($LD_{50}$=5 mM, 0.6 mM, respectively). In contrast, Kahalalide is cytotoxic to liver (AML-12), and kidney (NRX-52E) cells ($LD_{50}$=0.17 µM, 1.6 µM, respectively), and shows an intermediate toxicity to myelogenous stem cells (FDC-Pl, $LD_{50}$=14 µM). These data are in close agreement with in vivo toxicity data.

We have also found this drug to be neuxotoxic at high concentrations in our assay system and which correlates well with animal data showing neurotoxicity above the maximum tolerated dose (MTD). Using a fluorescent viability stain (ethidium homodimer and calccin AM, Molecular Probes) coupled with immunocytochemistry, we determined that ~10 µM Kahalalide is toxic to central nervous system (CNS) neurons (neurofilament positive) but spares astrocytes (glial fibrilary acidic protein positive) as well as sensory (substance P expressing) and motor (choline acetyl transferase positive) neurons in the spinal cord.

We conclude that Kahalalide F is a promising drug for the treatment of prostate cancer as its neurotoxicity is relatively mild at or below MTD levels. Further, preliminary data indicate that Kahalalide F may prove to be an ideal drug for treating neuroblastoma, if deliverable, due to its CNS neuron selectivity.

Example 4

Selective Antitumor Activity of Kahalalide F

Kahalalide F is a lysosomal poison with in vitro selectivity for hormone-independent prostate tumors, neu$^+$ (Her2 overexpressing) breast tumor cells and neuroblastomas. An extended MoA includes inhibition of erbB2 and blocking of the EGF receptor as well as inhibition of TGF a gene expression. Preclinical in vivo models have confirmed selectivity and sensitivity of hormone independent prostate tumors (PC-3 and DU-145) with a rodent MTD of 300 µg/kg BW. In vitro antiproliferative studies show equivalent $IC_{50}$ activities among certain prostate tumors (0.27 µM PC-3; 0.25 µM DU-145; 0.73 µM T-10, 0.24 µM DHM and 0.19 µM RB), but no activity to hormone-sensitive LnCAP. Other studies show selective, but slightly less potent $IC_{50}$ activities to neu$^+$ breast tumor cellc (2.5 µM SK-BR-3: 2 µM BT-474) and to a neuroblastoma cell line (1 µM BE(2)C). In vitro exposure studies demonstrate that KF is not schedule-dependent A minimum exposure of 1 hour is as potent as 48 hours, in most cases. Moreover, the immediate and delayed effects of cytotoxicity have the same pharmacodynamics and do not increase with treatment duration.

Phase 1 trials incorporating a daily times five, weekly schedule will begin soon in the evaluation of KF as a potential chemotherapeutic agent against solid tumors.

Example 5

Investigation of the Effects of Kahalalide F (PM92102) Against Human Tumor Specimens Taken Directly from Patients.

In vitro studies have shown activity of KF to cause cell swelling and ultimately death (Garcia-Rocha, et al., *Can Letters* 99:43-50). In the present study, fresh human tumor specimens were treated with KF to determine activity, utilizing the Human Tumor Cloning Assay. One hundred and four patient tumor specimens were treated with KF under 14-day continuous exposure at 0.01, 0.1, and 1.0 µM. Specimens were incubated in a 2-layer soft-agar cloning system at 37° C. and were removed on Day 14 for colony count. Colonies formed in the treated plates were compared to the number of colonies formed in the untreated control plates, and the percent colonies surviving at each concentration was calculated. The positive control plates contained the cell poison orthosodium vanadate (200 µg/ml). Among these specimens, approximately 30% were evaluable with appropriate negative and positive controls. In vitro responses (inhibitory response indicated by 50% survival) were observed in 16% (5/31). 19% (6/31), and 81% (25/31) of the specimens at 0.01, 0.1, and 1.0 µg/M, respectively. There was a positive relationship between concentration and response to KF, with a significant response (81%) at the higher concentration tested (1.0>0.1>0.01). Notable responses were seen in breast (100%), colon (75%), non-small cell lung (100%), and ovarian cancer specimens (91%). KF is a promising anticancer agent, to which a broad spectrum of tumors responded.

Example 6

Phase I and Pharmacokinetic Study of Kahalalide F in Patients with Advanced Androgen Refractory Prostate Cancer KF displays both in vitro and in vivo anti-tumor activity in various solid tumor models including breast, colon, non-small cell lung, and in particular prostate cancer. On the basis of its selectivity, KF is now further developed as a potential anticancer agent against androgen independent prostate tumors.

OBJECTIVE: In the present phase I clinical and pharmacokinetic (PK) study the toxicity profiles PK and anti-tumor activity of KF are investigated.

METHODS: KF is administered as an intravenous infusion over one hour, during five consecutive days every three weeks in patients with advanced or metastatic androgen refractory prostate cancer. On the basis of the MTD values defined in mice, a starting dose of 20 µg/m2/day was selected, which is equivalent to a total dose of 100 µg/m2. PK of KF were determined in plasma during the first course. Bioanalysis of KF was performed by LC-MS/MS. LDH, AF and especially PSA levels of each patient were also evaluated during the study to determine the activity of KF.

RESULTS AND DISCUSSION: At present 7 patients have been registered. Patients had a median age of 66 years (range 54-75). One patient per level was entered at 20, 40, 80 and 160 µg/m2/day. Due to transaminase elevation a number of 4 patients were entered at the current dose level, 320 µg/m2/day. The first patient of this study was re-entered at this dose level. Observed adverse events were rapidly reversible mild headache, fatigue, pain and local edema. The only drug related toxicity to date was a rapidly reversible CTC grade 3 ASAT that occurred at 320 µg/m2/day. PK revealed a linear relationship between dose and AUC over the whole dose range. Total plasma clearance was 267 mL/min (±115) and the terminal half-life of intravenous KF in these patients was 0.46 h (±0.13). Maximum plasma concentrations reached at the current dose level (35-50 ng/mL) are potentially active for prostate cancer in the clonogenic tumor assay (activity from 15 ng/mL). Thus far, the schedule is well tolerated. One patient showed a significant decrease in PSA level (>50%) associated to clinical improvement (pain relief). Two additional patients experienced minor PSA reductions, one still ongoing after two cycles. The maximum tolerated dose has not been reached yet and the study is ongoing.

Example 7

Kahalilide F is cytotoxic to dedifferentiated and mesenchymal chodrosarcomas, CHSAs, and osteosarcomas, OSAs, as well as to hepatocellular and prostate carcinoma cells. It did not significantly inhibit the growth of CHSA and OSA cells, and was able to elicit a cytotoxic effect even if exposed to cells for as short as 10 minutes.

The invention claimed is:

1. A formulation of kahalalide F consisting essentially of a lyophilised mix of kahalalide F, a non-ionic surfactant, an organic acid and a bulking agent.

2. A reconstituted solution prepared from the formulation of claim 1.

3. A diluted reconstituted solution comprising the reconstituted solution according to claim 2 when diluted with 0.9% saline to a concentration effective for infusion of the kahalalide F.

4. A kit comprising a formulation of kahalalide F consisting essentially of a lyophilised mix of kahalalide F, a non-ionic surfactant, an organic acid and a bulking agent-together with instructions for dilution with a reconstitution solution of a mix of emulsifying solubiliser, alkanol and water.

5. The kit of claim 4, together with a supply of the reconstitution solution.

6. A reconstituted solution of kahalalide F consisting essentially of a mix of kahalalide F, a non-ionic surfactant, an organic acid and a bulking agent, when reconstituted using a reconstitution solution of a mix of emulsifying solubiliser, alkanol and water.

7. A diluted reconstituted solution comprising the reconstituted solution according to claim 6 when diluted with 0.9% saline to a concentration effective for infusion of the kahalalide F.

* * * * *

UNITED STATES PATENT AND TRADEMARK OFFICE
CERTIFICATE OF CORRECTION

| | | |
|---|---|---|
| PATENT NO. | : 7,473,681 B2 | Page 1 of 1 |
| APPLICATION NO. | : 10/399571 | |
| DATED | : January 6, 2009 | |
| INVENTOR(S) | : Faircloth et al. | |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 519 days Delete the phrase "by 519 days" and insert -- by 769 days --

Signed and Sealed this

Twenty-seventh Day of April, 2010

David J. Kappos
*Director of the United States Patent and Trademark Office*